United States Patent [19]
Cox et al.

[11] 4,332,225
[45] Jun. 1, 1982

[54] INTERNAL COMBUSTION ENGINE WITH OXYGEN SENSOR HEATER CONTROL

[75] Inventors: Francis G. Cox, Grand Blanc, Mich.; William J. Ricketts, Anderson, Ind.

[73] Assignee: General Motors Corporation, Detroit, Mich.

[21] Appl. No.: 192,990

[22] Filed: Oct. 2, 1980

[51] Int. Cl.³ .......................... F02B 3/00; F02M 7/00
[52] U.S. Cl. .................................. 123/440; 123/489; 204/195 S
[58] Field of Search .................. 123/440, 489; 60/276, 60/285; 204/195 S, 15; 73/23

[56] References Cited

U.S. PATENT DOCUMENTS

| | | | |
|---|---|---|---|
| 3,616,274 | 10/1971 | Eddy | 204/195 S |
| 3,738,341 | 6/1973 | Loos | 123/440 |
| 3,915,135 | 10/1975 | Kushida et al. | 204/195 S |
| 3,946,198 | 3/1976 | Foote | |
| 3,948,081 | 4/1976 | Wessel et al. | 73/23 |
| 4,129,099 | 12/1978 | Howarth | 204/195 S |
| 4,130,095 | 12/1978 | Bowler et al. | 123/440 |
| 4,167,163 | 9/1979 | Moder | 204/195 S |
| 4,170,967 | 10/1979 | Wessel et al. | 123/440 |

Primary Examiner—P. S. Lall
Attorney, Agent, or Firm—Robert M. Sigler

[57] ABSTRACT

An internal combustion engine with a closed loop air/fuel ratio control utilizes a heated zirconia sensor, the sensor including a resistance heater element connected to receive electric current from the vehicle battery, the sensor having an internal parasitic capacitance and being characterized by a leakage current path between the heater element and the capacitance. The sensor output voltage is sampled by the closed loop control periodically and current is supplied to the heater element only during periods which end a predetermined time before each such sampling so that any charge on the capacitance may discharge before it affects the sampled voltage. Within each period, the current may be duty cycle modulated in response to vehicle battery voltage to maintain a constant average power to the heater element when heat is required.

2 Claims, 6 Drawing Figures

INTERNAL COMBUSTION ENGINE WITH OXYGEN SENSOR HEATER CONTROL

BACKGROUND OF THE INVENTION

This invention relates to a control for the heater of a heated oxygen sensor in an internal combustion engine closed loop air/fuel ratio control, and especially for such a control utilizing a zirconia oxygen sensor or its equivalent. Such air/fuel ratio controls are becomming ever more common in emission control systems wherein they help maintain a substantially stoichiometric air/fuel ratio to the engine so that the exhaust gases may be successfully treated by a three-way catalytic converter.

Such closed loop air/fuel ratio control systems generally utilize such a sensor exposed to the exhaust gases from the engine and sensitive to at least one component thereof. A typical such sensor is the zirconia oxygen sensor, which operates as an electrochemical cell and, when warm, generates a typical output voltage of 800 to 1,000 millivolts in the absence of oxygen that would be characteristic of exhaust gases from an air/fuel ratio richer than stoichiometric and generates a typical output voltage of 0 to 200 millivolts in the presence of oxygen characteristic of exhaust gases obtained from an air/fuel mixture leaner than stoichiometric.

However, the internal impedance and generated voltage of such sensors varies greatly with temperature, such that the sensor must be heated far above normal atmospheric environmental temperatures to generate a useable output voltage. In most cases, the heat of the exhaust gases from the engine is sufficient to heat the sensor to the required operating temperature and maintain such temperature; however, when an engine is started from a cold condition there is a period of time before the sensor becomes sufficiently heated to operate correctly in the control system. In addition, different engines vary considerably in exhaust temperature; and some engines may have an exhaust temperature so cool that the sensor temperature falls below its desired operating temperature during some conditions of engine operation, such as prolonged idle. Most closed loop air/fuel ratio control systems provide for such periods of sensor unreliability due to insufficient sensor temperature by substituting open loop backup controls at the proper times. However, in most cases, such open loop controls do not provide the efficiency of emission reduction provided by the closed loop system; and it therefore may be desirable to minimize such periods of open loop control if it is necessary to increase the overall efficiency of the emission control.

One method of minimizing the periods of sensor unreliability due to low sensor temperature is the use of an electric heater to heat the oxygen sensor directly and thus control its operating temperature. A good example of an oxygen sensor of the type described above which includes a heater element is shown in the U.S. Pat. No. 4,178,222 issued to Michael P. Murphy et al on Dec. 11, 1979. The incorporation of the heater directly into the sensor package provides a compact, self-contained unit and good heat conduction between the heater element and sensor. However, the variation in exhaust temperature over time from a single engine and the efficiency of heat conduction in such a sensor design make it undesirable, in most cases, for the heater to be operated at all times. It is most desirable to operate the heater only when sensor temperature falls below a predetermined temperature or when the engine is being operated in a condition which makes it likely that the sensor temperature would fall below the predetermined temperature.

In addition, a zirconia oxygen sensor is characterized by a charge storage effect when supplied with current from an external source. This effect may be described in terms of an internal capacitance in parallel with its output terminals. When a heater element is combined in a single package with such a sensor, it is difficult to avoid a leakage current path from the heater to the sensor terminals in either the sensor itself or the connecting means. This leakage current path may have a very high resistance; but, nevertheless, the heater current may be sufficient to appreciably charge the sensor capacitance and thus affect the sensor output voltage. This further supports the desirability, at least in some systems, of not operating the oxygen sensor heater at all times.

SUMMARY OF THE INVENTION

It is an object of this invention to provide a heater control for a heated oxygen sensor in an internal combustion engine closed loop air/fuel ratio control wherein operation of the heater does not adversely affect the sensed output voltage of the sensor.

This and other objects are realized in an apparatus including a closed loop air/fuel ratio control system effective to periodically sample the oxygen sensor voltage at predetermined intervals, electrical power supply means effective to provide electric current to a resistive heater element in the oxygen sensor during heater control signal pulses and means effective to generate a heater control signal pulse beginning shortly after each periodic sampling of the oxygen sensor output voltage and ending at least a predetermined minimum time before the next sampling of the oxygen sensor output voltage. The predetermined minimum time is sufficient to allow discharge of the oxygen sensor stray capacitance to rid the sensor of any such charge due to leakage current from the heater element during the previous heater control signal pulse. In addition, the heater control signal pulses may be of variable width in a pulse width modulated power control, wherein the maximum pulse width still provides the predetermined minimum off time before the next sampling of the oxygen sensor output voltage. Further details and advantages of the invention will be apparent from the accompanying drawings and following description of a preferred embodiment.

DESCRIPTION OF THE PREFERRED EMBODIMENT

Figure 1:
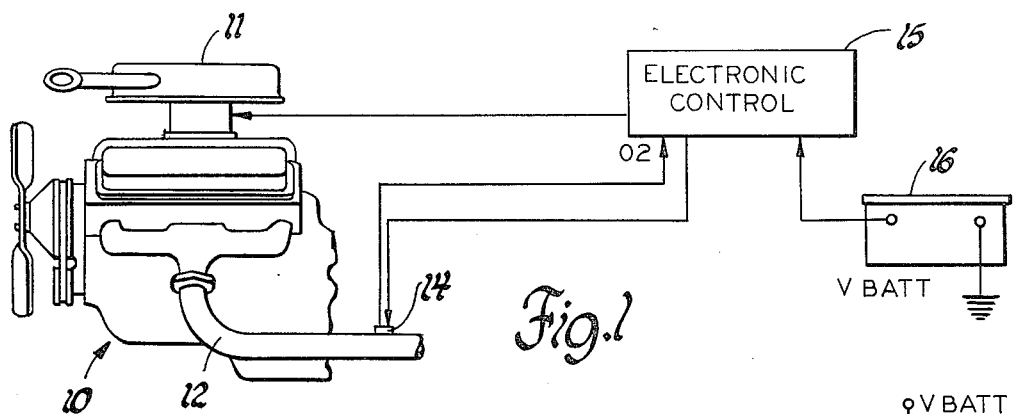
FIG. 1 is a schematic drawing of an internal combustion engine with a closed loop air/fuel ratio control according to this invention.

Referring to FIG. 1, an internal combustion engine 10 includes air/fuel induction apparatus 11 which may be any of a variety of known carburetors or fuel injection systems which provide for an electrical control of air/fuel ratio to the engine. Further included with engine 10 is an exhaust conduit 12 in which is located an oxygen sensor 14. Sensor 14 is of the zirconia cell type as identified above, including an electrical resistive heater element; an example is shown in the previously mentioned Murphy et al patent. An electronic control 15 receives electrical power from the vehicle battery 16 and further receives an oxygen sensor output voltage signal from sensor 14. An electronic control 15 supplies a heater control current to the heater element of sensor 14 and an air/fuel ratio control signal to air/fuel induction apparatus 11.

Figure 2:
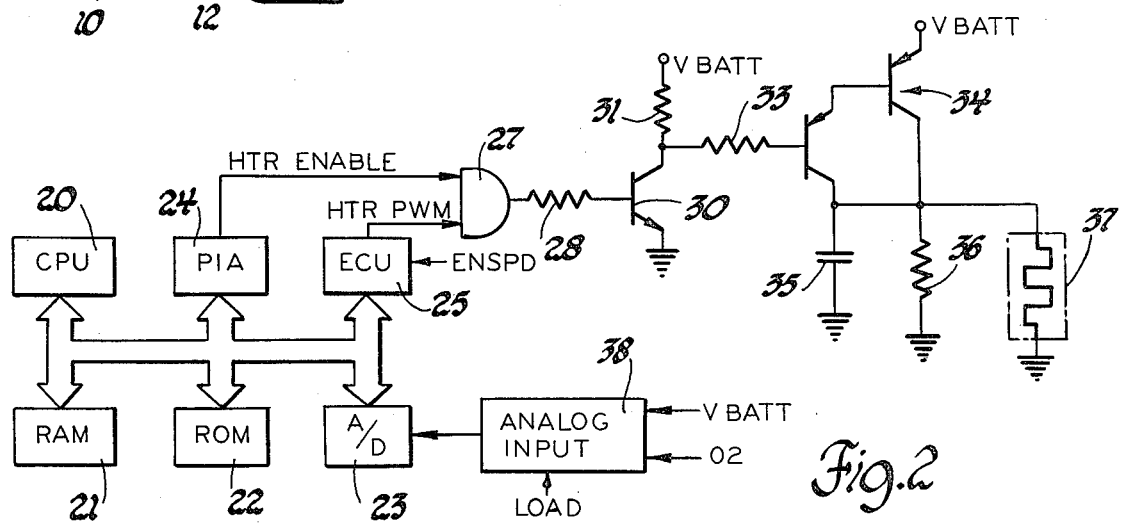
FIG. 2 is a drawing partly schematic and partly in circuit form of part of an electronic control for use with the engine of FIG. 1.

FIG. 2 shows a portion of electronic control 15 relevant to the description of this invention. Electronic control 15 includes a digital computer comprising a central processing unit (CPU) 20, a random access memory (RAM) 21, a read only memory (ROM) 22, an analog to digital converter (A/D) 23, a peripheral interface adapter (PIA) 24 and an electronic control unit (ECU) 25. These elements, with the exception of ECU 25, are well known elements in the digital electronic field and are interconnected with the appropriate buses and control lines as a functioning digital computer. An example of such elements is the Motorola 6800 series of microprocessor and supporting chips. In this application, ROM 22 is used to store a program for the operation of the computer according to this invention; RAM 21 is used for temporary storage; A/D converter 23 is used to convert analog inputs of vehicle battery, oxygen sensor and load sensor voltage to digital form; and peripheral interface adaptor 24 is used as an output port to latch a heater enable output signal. Electronic control unit 25 is an input/output device including a downcounter which can store a pulse width number from the computer and be triggered by a signal from the computer into counting down from that number at a predetermined counting rate, thus generating an output pulse with a duration proportional to the number. ECU 25 further includes a digital input for ENSPD from the engine distributor, which comprises a pulsed engine speed signal.

The heater enable signal from PIA 24 and the heater pulse width signal from ECU 25 are supplied to the inputs of an AND gate 27, the output of which is connected through a resistor 28 to the base of an NPN transistor 30. The emitter of transistor 30 is grounded; and the collector is connected through a resistor 31 to vehicle battery 16 and through a resistor 33 to the base of a PNP Darlington transistor pair 34. Darlington transistor pair 34 has an emitter connected to the vehicle battery 16 and a collector connected in parallel through a capacitor 35, a resistor 36 and heater element 37 of sensor 14 to ground. An analog input buffer circuit 38 receives inputs from the vehicle battery 16, oxygen sensor 14 and a load indicating parameter sensor such as a manifold absolute pressure, vacuum or throttle position sensor and supplies the buffered outputs to A/D converter 23.

Figure 3:
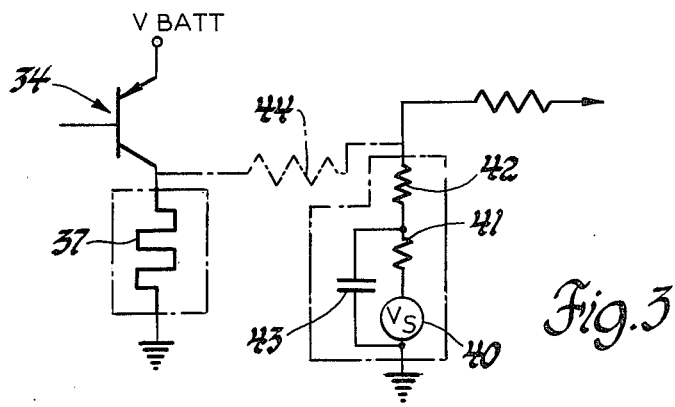
FIG. 3 is an equivalent circuit diagram of a heated oxygen sensor showing the internal capacitance and leakage current path between the sensor and the heater element.

As shown in FIG. 3, an oxygen sensor can be described as a voltage source 40 in series with internal impedances 41 and 42, voltage source 40 and impedance 41 having a parallel internal parasitic capacitance 43. Heater element 37 is included in the same package with oxygen sensor 14 in good thermal contact therewith and a single connector package connects the heater and sensor terminals to connecting wires. Therefore, in spite of the best practical insulation between heater element 37 and the rest of oxygen sensor 14, a leakage current path, indicated as impedance or resistor 44 in FIG. 3, will exist between the ungrounded end of heater element 37 and the ungrounded terminal of oxygen sensor 14. This resistance might be on the order of 10-20 megohms, but could be lower under unfavorable environmental conditions. A 14 volt vehicle battery may therefore provide a charging current through impedances 44 and 41 which cannot be ignored.

Figure 4:
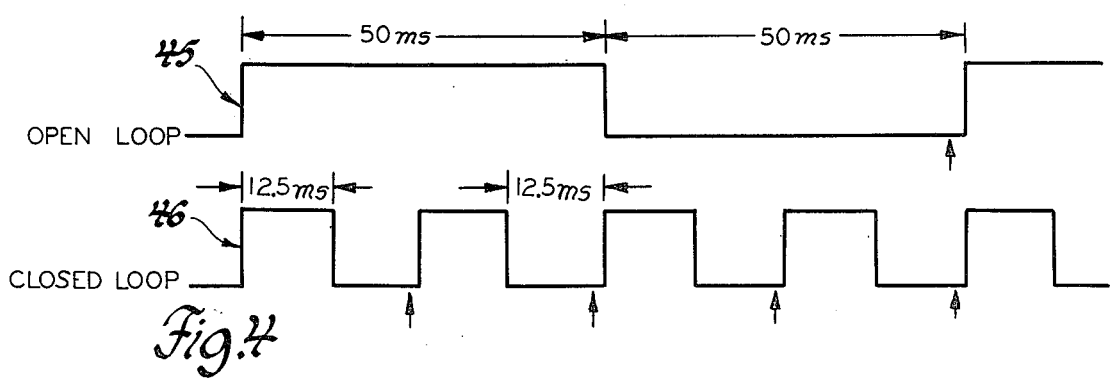
FIG. 4 includes a pair of timing diagrams illustrating the operation of the circuit of FIG. 2 during open and closed loop operation.

Therefore, as shown in the waveforms of FIG. 4, the current to heater element 37 is shut off a certain predetermined time before the reading of the sensor by the computer, which is done on a periodic basis. This allows any excess charge on capacitance 43 to discharge so that the output voltage of the sensor accurately shows the voltage of voltage source 40. A 50 millisecond time has been determined to be sufficient for a cold sensor in an open loop condition, where impedances 41 and 42 are high.

Waveform 45 shows a typical waveform for the heater enable signal provided to AND gate 27 during open loop operation. During this time, the oxygen sensor signal is read only once every 100 milliseconds to determine whether the sensor is ready to assume control under closed loop operation. A fifty percent duty cycle yields an on time of 50 milliseconds and an off time of 50 milliseconds as shown in waveform 45.

Referring to waveform 46, it can be seen that the oxygen sensor is sampled four times as often, or once every 25 milliseconds, during closed loop operation, since the sensor signal is actually being used to control the air/fuel ratio. In this case, the minimum off time before each sampling is 12.5 milliseconds, which also yields a maximum duty cycle of fifty percent.

In this embodiment, it is desired to vary the duty cycle in response to the sensed voltage of the vehicle battery to maintain a constant average power output to the heater element 37. This means that the duty cycle should be the same for closed loop and open loop operation. This, plus the slower discharge of capacitance 43 when the sensor is cold, explains the longer minimum off time during open loop operation. The duty cycle shown in waveforms 45, 46 is the maximum allowed duty cycle as the duty cycle is varied to maintain the constant power to the heater element 37. The actual duty cycle is computed from measured vehicle battery voltage and supplied as the heater pulse width (HTRPWM) to AND gate 27 from ECU 25. The heater enable (HTR ENABLE) signal from PIA 24 to AND gate 27 is supplied as the appropriate one of waveforms 45 and 46, but only when necessary as determined from an engine load indication in a manner to be described at a later point in this specification. Only when both signals are high will transistor 30 be turned on. When transistor 30 is turned on, Darlington transistor pair 34 is also turned on to supply current to heater element 37.

The full operation of the system will be described with reference to the flow charts of FIGS. 5 and 6. These flow charts are, of course, only portions of the complete engine control flow charts, which would include air/fuel ratio control and possibly other controls. However, they contain the steps in the flow charts or programs that are necessary to the operation of sensor heater control.

Figure 5:
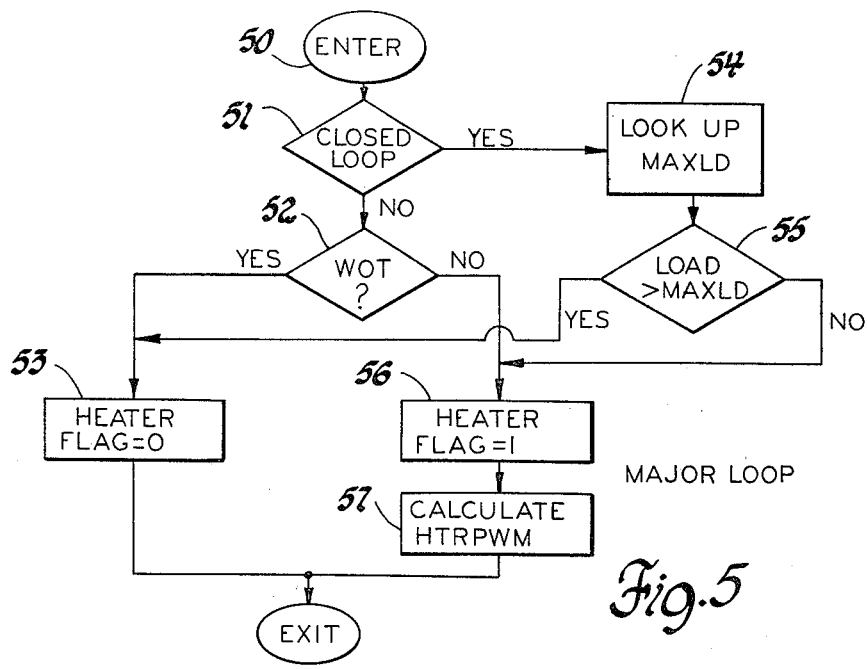
FIGS. 5 and 6 show flow charts in block diagram form illustrating the operation of this invention.

The major loop of the computer, initiated once every 100 milliseconds, is illustrated in the flow chart of FIG. 5. This portion of the major loop program is entered at step 50 and passes to decision point 51, wherein a flag is checked to see whether the system is operating in closed loop control. If the answer is no, the program proceeds to decision point 52, wherein another flag is checked to see whether the engine is operating in a wide open throttle or acceleration mode. If the answer is yes, the program proceeds to step 53, in which a heater flag is set to 0, after which the computer exits from this portion of the program.

If decision point 51 indicates closed loop control, the program proceeds to step 54 in which the latest value of engine speed is used as an entry to a lookup table in which several values of MAXLD are stored as a function of engine speed ranges. MAXLD is a number representing the value of engine load below which, at a given engine speed, it is predicted that the sensor will require supplemental heating by means of element 37. Such values are calculated during the calibration of a particular engine type in its initial design and stored in ROM 22. From step 54, the program proceeds to decision point 55 in which the most recent value of a load indicating engine parameter such as manifold absolute pressure or throttle angle is compared with the value of MAXLD obtained from the table lookup. If the actual load indicating parameter value is greater than MAXLD, the program proceeds to step 53 and sets the heater flag to 0. The two possible paths through the flow chart described above illustrate the engine conditions of wide open throttle, open loop operation and high load closed loop operation, neither of which calls for sensor heating. If desired, steps 54 and 55, as well as the MAXLD memory space, could be replaced by an intake vacuum switch with an appropriate input to CPU 20 to set a flag when load is low and a flag checking step replacing steps 54 and 55.

If neither closed loop operation nor wide open throttle are indicated, the system is in open loop operation, probably due to insufficient sensor temperature. In addition, if closed loop operation is indicated but the indicated load is less than or equal to MAXLD, insufficient sensor heating from exhaust is indicated, which may eventually lead to open loop operation if continued. In either case, from decision points 52 or 55, the program proceeds to step 56 in which the heater flag is set to 1 and then proceeds to step 57 in which the heater pulse width is calculated. In this embodiment, this pulse width is varied on a duty cycle basis according to the measured value of vehicle battery voltage to produce a constant average power to heater element 37 at times when the current pulses are being supplied thereto. Thus the duty cycle is calculated according to the equation $DC = K1/(VBATT - K2)^2$, wherein DC is duty cycle, K1 is a first calibration constant which will produce a desired average power in a given heater impedance with a maximum duty cycle of 50% at some minimum desired value of VBATT (which may be the lowest voltage level at which the control system effectively operates) and K2 is a second calibration constant representing the portion of VBATT dropped outside the heater impedance. The actual pulse width may be obtained for open or closed loop operation by multiplying the duty cycle times either 100 or 25 milliseconds, respectively, depending on the condition of the closed loop flag. The number is then temporarily stored in an appropriate memory location in RAM 21 or immediately output to ECU 25; and the program exits from this portion thereof.

Figure 6:
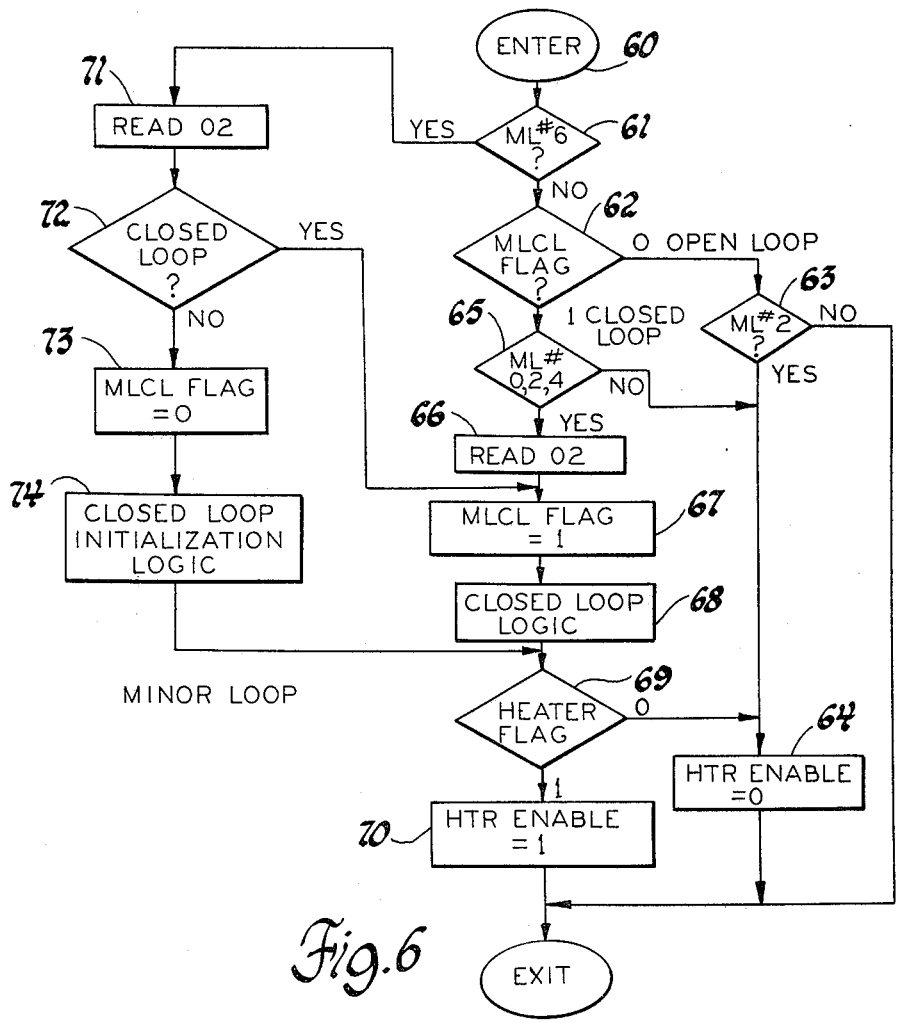

The minor loop is run every 12.5 milliseconds, with the portion of the minor loop concerned with a sensor heater control shown in FIG. 6. In a different part of the minor loop program, not shown, a count of consecutive minor loops is kept in a memory location in RAM 21. This count is incremented from 0 to 7 and reset to 0 in a repeated manner so that minor loops are numbered and run in repeated series of 8, which correspond to the time of one major loop.

The portion of the minor loop shown in FIG. 6 is entered at step 60 and proceeds to decision point 61, in which it is determined whether this is minor loop number 6. If it is not, the program proceeds to decision point 62, in which the minor loop closed loop (MLCL) flag is examined. This flag would ordinarily be initially set at 0 to indicate open loop operation. Therefore the program would proceed to decision point 63, in which it is determined whether this is minor loop number 2. If not, the computer exits from this portion of the minor loop program. If decision point 63 indicates that this is minor loop number 2, the program proceeds to step 64, in which the heater enable output is set to 0 through PIA 24, and then exits this portion of the program.

Returning to decision point 62, if the MLCL flag is set, the program proceeds to decision point 65, which determines whether this is minor loop number 0, 2, or 4. If not, that is, if this is minor loop number 1, 3, 5 or 7, the computer proceeds to step 64 to output heater enable signal 0. If so, however, the program proceeds to step 66 in which the 02 input signal is read. After step 66, the program proceeds to step 67 and sets the MLCL flag to 1. After step 67, the program proceeds to step 68 in which the closed loop logic is performed. In this step, the 02 sensor signal is examined and processed for use in the closed loop fuel control system. Since the details of this examination and processing are unimportant to the invention claimed, such details are omitted from this description. Examples of such logic are known or obvious from the prior art.

After step 68, the program proceeds to decision point 69, in which the heater flag, which was set to 0 or 1 in the major loop, is examined. If it is 0, the program proceeds to step 64 to set the heater enable output to 0. If the heater flag is 1, however, the program proceeds to step 70 in which the heater enable output is set to 1; then the computer exits this portion of the program.

Returning to decision point 61, if this is minor loop number 6, the program proceeds to step 71, in which the 02 sensor signal is read. Next the program proceeds to decision point 72, in which it is determined whether the system is in closed loop or open loop operation. If in closed loop operation, the program proceeds next to step 67, already described. If not, however, the program proceeds to step 73, in which the MLCL flag is set to 0 and then to step 74, which is the closed loop initialization logic. As in the case of the closed loop logic, already mentioned, the details of the closed loop initialization logic are not important to an understanding of this invention and they are therefore omitted. After this step, the program proceeds to decision point 69, already described.

To provide a better understanding of the dynamics of the minor loop shown in FIG. 6, the operation of the minor loop will be described in a different manner. The path followed by the computer through the minor loop will depend on whether the system is in closed loop or open loop operation and also on the number of the minor loop 0 to 7. In open loop operation, the computer will proceed during minor loop number 2 through steps and decision points 61, 62, 63 and 64 to set the heater enable signal to 0. It will further proceed during minor loop number 6 through steps and decision points 61, 71, 72, 73, 74, 69 and 70 to set the heater enable signal to 1. During all other minor loops, the program will proceed through decision points 61, 62 and 63 to exit without changing the heater enable output. Thus the heater enable output is switched between 0 and 1 every four minor loops, or every 50 milliseconds, during open loop operation. In addition, it can be seen that the oxygen sensor signal is read on minor loop number 6 during open loop operation just before the heater enable output is set to 1. This operation is illustrated by the waveform 45 in FIG. 4.

During closed loop operation, the computer proceeds, during minor loops number 1, 3, 5 and 7, through steps and decision points 61, 62, 65 and 64 to reset the heater enable signal to 0. During minor loops number 0, 2 and 4, the program proceeds by decision points and steps 61, 62, 65, 66, 67, 68, 69 and 70 to first read the oxygen sensor signal and then set the heater enable output to 1. During minor loop number 6 the program accomplishes the same result by a path through steps and decision points 61, 71, 72, 67, 68, 69 and 70. Thus, in closed loop operation, the program switches the heater enable signal between 0 and 1 every 12.5 milliseconds, with the oxygen sensor signal being read just before each change from 0 to 1.

Of course, the above description assumes that the heater flag was set to 1 in the major loop. If not, decision point 69 ensures that the heater enable output signal will be reset to 0 at all times. It should be noted that the HTRPWM signal from ECU 25 must be coordinated with the HTR ENABLE signal from PIA 24 so that the former is output during even numbered minor loops during closed loop operation and during minor loops 6, 7, 0 and 1 during open loop operation.

Although the above-described embodiment is preferred, equivalents will occur to those skilled in the art. Therefore, the invention should be limited only by the claims which follow.

The embodiments of the invention in which an exclusive property or privilege is claimed are defined as follows:

1. In combination:
   an internal combustion engine having fuel supply and exhaust means;
   an oxygen sensor in said exhaust means, said sensor being effective to generate an output voltage in response to engine exhaust content, said sensor further being characterized by an associated internal capacitance and including a separate resistive heater element with a leakage current path between the heater element and sensor stray capacitance;
   closed loop control means effective to periodically sample the oxygen sensor output voltage at predetermined times and generate therefrom a fuel control signal for application to the fuel supply means;
   electric power supply means characterized by an output supply voltage and effective to provide electric current to the resistive heater element during received heater control signal pulses with consequent charging of the sensor internal capacitance through the leakage current path; and
   means effective to generate the heater control signal pulses, each pulse beginning shortly after a sampling of the oxygen sensor output voltage and ending at least a predetermined minimum time before the next sampling of the oxygen sensor output voltage, whereby the charge on the oxygen sensor internal capacitance due the leakage current from the heater element during each heater control signal pulse may discharge prior to the subsequent sampling of the oxygen sensor output voltage and thus not adversely affect the sampled voltage.

2. In combination:
   an internal combustion engine having fuel supply and exhaust means;
   an oxygen sensor in the exhaust means, said sensor being effective to generate an output voltage in response to engine exhaust content, said sensor further being characterized by an associated internal capacitance and including a separate resistive heater element with a leakage current path between the heater element and internal capacitance;
   closed loop control means effective to periodically sample the oxygen sensor output voltage at predetermined times and generate therefrom a fuel control signal for application to the fuel supply means;
   electric power supply means characterized by a variable output supply voltage and effective to supply electric current to the resistive heater element during received heater control signal pulses with consequent charging of the sensor internal capacitance through the leakage current path;
   means effective to generate the heater control signal pulses, each pulse beginning shortly after a sampling of the oxygen sensor output voltage and ending at least a predetermined time before the next such sampling, said means being further responsive to the output supply voltage of the electric power supply means to vary the duration of the heater control signal pulses to maintain a constant average power in the resistive heater element, whereby a controlled power is supplied to the sensor heater element in pulses allowing discharge of the sensor internal capacitance before each sampling of the sensor voltage for an accurate sampling thereof.

* * * * *

UNITED STATES PATENT AND TRADEMARK OFFICE
CERTIFICATE OF CORRECTION

PATENT NO. : 4,332,225
DATED : June 1, 1982
INVENTOR(S) : Francis G. Cox et al

It is certified that error appears in the above—identified patent and that said Letters Patent is hereby corrected as shown below:

Column 8, line 19, "the" should read -- to --.

Signed and Sealed this

Twenty-first Day of September 1982

[SEAL]

Attest:

GERALD J. MOSSINGHOFF

Attesting Officer

Commissioner of Patents and Trademarks